United States Patent [19]
Quake

[11] Patent Number: 6,002,471
[45] Date of Patent: Dec. 14, 1999

[54] HIGH RESOLUTION SCANNING RAMAN MICROSCOPE

[75] Inventor: Stephen R. Quake, Pasadena, Calif.

[73] Assignee: California Institute of Technology, Pasadena, Calif.

[21] Appl. No.: 08/964,295

[22] Filed: Nov. 4, 1997

Related U.S. Application Data

[60] Provisional application No. 60/030,026, Nov. 4, 1996.

[51] Int. Cl.[6] .......................... G01N 21/64; G01N 21/65; G01B 11/24
[52] U.S. Cl. ........................... 356/73; 356/301; 356/318; 356/376; 250/458.1
[58] Field of Search ..................................... 356/301, 317, 356/318, 73, 376; 250/458.1, 459.1, 461.1, 461.2

[56] References Cited

U.S. PATENT DOCUMENTS

| | | | |
|---|---|---|---|
| 5,212,386 | 5/1993 | Gratton et al. | 356/317 |
| 5,257,085 | 10/1993 | Ulich et al. | 356/301 |
| 5,479,024 | 12/1995 | Hillner et al. | 250/458.1 |

OTHER PUBLICATIONS

Shuming Nie and Steven R. Emory, Probing Single Molecules and Single Nanoparticles by Surface–Enhanced Raman Scattering, Feb. 21, 1997, Science vol. 275.

Katrin Kneipp, Yang Wang, Harold Kneipp, Lev T. Perelman, Irving Itzkan, Ramachandra R. Dasari, and Michael S. Feld, Single Molecule Detection Using Surface–Enhanced Raman Scattering (SERS), Mar. 3, 1997, The American Physical Society, Physical Review Letters vol. 78 No. 9.

F. Zenhausern, Y. Martin, H. K. Wickramasinghe, Scanning Interferometric Apertureless Microscopy: Optical Imaging at 10 Angstrom Resolution, Aug. 25, 1995, Science vol. 269.

*Primary Examiner*—F. L. Evans
*Attorney, Agent, or Firm*—Fish & Richardson P.C.

[57] ABSTRACT

A method of obtaining high-resolution spectroscopic information from a scanning microscope. An optical beam is directed at a sample and light emitted from the sample (e.g., from Raman scattering or fluorescence) is collected. Resolution is improved by supporting a tiny conductive element (e.g., a silver particle) from a probe located within the optical beam area. The conductive element enhances the light emitted from molecules in the vicinity of the probe. The invention provides the high spatial resolution of microscopes such as the AFM with the high chemical detection sensitivity of surface enhanced Raman spectroscopy. This combination allows the isolation and differentiation of single molecules on surfaces of nanostructures.

52 Claims, 4 Drawing Sheets

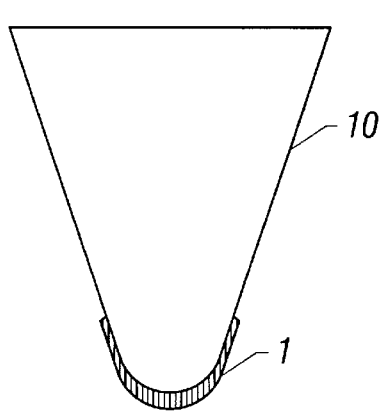
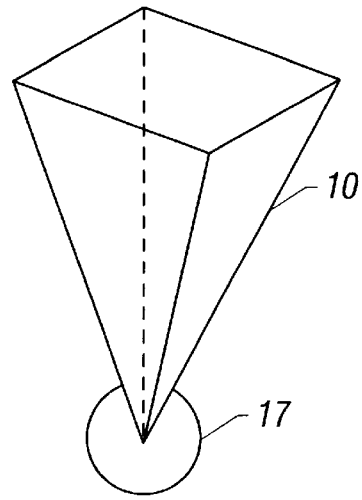
FIG. 4          FIG. 5
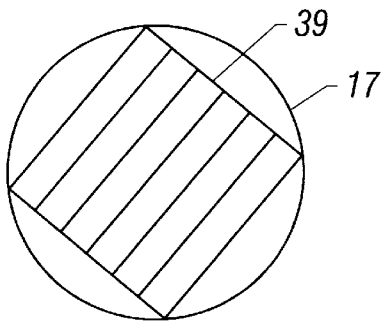
FIG. 6
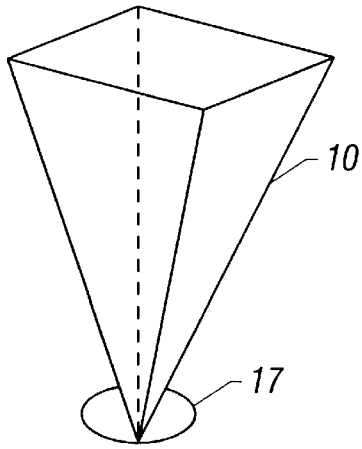
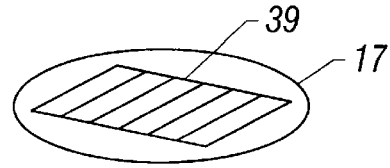
FIG. 7          FIG. 8

HIGH RESOLUTION SCANNING RAMAN MICROSCOPE

CROSS REFERENCE TO RELATED APPLICATIONS

This application is a continuation-in-part of provisional application Ser. No. 60/030,026, field Nov. 4, 1996.

BACKGROUND OF THE INVENTION

Single molecule spectroscopic techniques are becoming very sophisticated, and are now revealing information that was not possible to discern from bulk experiments. For example, polymer physics experiments with single molecules of DNA have permitted detailed study of non-equilibrium dynamics, measurement of non-linear forces of highly extended polymers, and the first direct measurement of the normal mode relaxation structure of a polymer.

Scanning probe microscopy has had a renaissance in recent years. Following the invention of the scanning optical microscope, the atomic force microscope (AFM) and near field scanning optical microscope were invented. These instruments have found many applications in biology, chemistry, physics and materials science. Recently, a far field optical interferometer was combined with an AFM in order to create a super-resolution scanning optical microscope. Contrast is generated by induced dipole-dipole interactions between the tip and sample, so that the resolution is limited only by the size of the tip. This information is encoded in the scattered electric fields and measured with an interferometer. It is an excellent method for taking extremely high resolution images of objects on a surface, but does not provide much detail for distinguishing different types of objects or chemical species. There have been some variations on the AFM, called chemical force microscopy, but these devices can only identify adhesion forces between particular ligands.

Raman spectroscopy has a long history of utility in the identification of molecular vibrational modes. In practice, Raman spectra are often used to distinguish different molecular species. However, the probability of Raman scattering is low (Raman cross sections are exceedingly small, $10^{-30}$ cm$^2$ for CN), which limits the applicability of the technique. In 1974 it was discovered that roughened silver surfaces caused enhancements of Raman scattering by 6–7 orders of magnitude. This effect became known as surface enhanced Raman scattering (SERS) and was explained with the concept of field enhancement from classical electrodynamics. Numerous experiments and theoretical studies have been performed to confirm this picture. The key feature necessary for SERS is to have a surface roughness of characteristic size 10–100 nm, made of a material whose dielectric constant satisfies a certain resonance condition. It turns out that silver is one of the best materials for studying SERS with visible light, and many SERS studies have used silver surfaces. Both Raman and SERS Raman microprobes and microscopes have been constructed, but their resolutions are on the order of 1 mm and require a large amount of sample.

In spite of the enhancement from SERS, a single molecule will Raman scatter only a small number of photons, and photon counting detection scheme must be used. A comparable situation is found in the detection of single fluorescent dye molecules. The field of single molecule fluorescence has seen tremendous growth over the past few years, and there are now a plethora of techniques with which to detect the photons emitted from a single dye molecule. The detectors are typically avalanche photodiodes, and a wide variety of background reduction techniques have been used, including confocal optics, two photon excitation and evanescent wave excitation.

SUMMARY OF THE INVENTION

The invention provides a method of obtaining high-resolution spectroscopic information from a scanning microscope. An optical beam is directed at a sample and light emitted from the sample (e.g., from Raman scattering or fluorescence) is collected. Resolution is improved by supporting a tiny conductive element (e.g., a silver particle) from a probe located within the optical beam area. The conductive element enhances the light emitted from molecules in the vicinity of the probe. The invention provides the high spatial resolution of microscopes such as the AFM with the high chemical detection sensitivity of surface enhanced Raman spectroscopy. This combination allows the isolation and differentiation of single molecules on surfaces of nanostructures.

In preferred embodiments, the invention may include one or more of the following features.

The probe may be an Atomic Force Microscope (AFM) probe, and AFM topographic information may be combined with the high-resolution spectroscopic information.

The area illuminated by the optical beam may be greater (e.g., at least ten times greater) than the area in which enhancement occurs in the vicinity of the conductive element.

The distance between the conductive element and the surface of the sample may be controlled.

The support stage may have three dimensional scanning capability.

The surface of the conductive element may have a curvature of less than or equal to 20 nm.

The probe may include carbon nanotubes with a radius of curvature of less or equal to 5 nm.

The probe may have pyramidal geometry.

The probe may include silicon nitride.

The conductive element may include a conductive layer.

The conductive layer may be a conductive particle (or particles), which could be a sphere or an ellipsoid. The conductive particle may be a colloidal silver particle attached by surface adhesion forces on the probe.

The conductive element may include metal particles selected from the group consisting of silver, gold, platinum, copper, and aluminum.

The conductive element may include multiple metallic layers.

The probe may be single crystalline silicon or carbon.

A photon counting avalanche photodiode may be used to collect the emitted light.

The probe may oscillate in a tapping mode and the tapping frequency be used to modulate the detection signal by lock-in detection methods.

The optical apparatus may comprise a spectrometer, e.g., a diffraction grating and an image intensified charged coupled device (CCD) camera (which may be cooled).

The invention may be used for sequencing DNA, by obtaining surface enhanced Raman scattering images of the four individual DNA bases.

The invention may be used for in situ diagnostic quality control of nanostructural electronic devices, by scanning the probe over the surface of the nanostructures and obtaining surface enhanced Raman scattering spectra.

The invention may used to detect ultra-low level chemical components in a mixture by obtaining surface enhanced Raman scattering spectra.

In a second aspect, the invention features forming an AFM probe by forming a pyramidal mold in a silicon crystal by etching the silicon crystal through a rectangular (e.g., square) mask; filling the mold with silicon nitride; and removing the mask and silicon crystal by etching and leaving a pyramidal shaped silicon nitride tip. The tip of the probe is preferably coated with a conductive layer or with one or more conductive particles (e.g., silver particles).

Other features and advantages of the invention will be apparent from the following description of preferred embodiments, and from the claims.

BRIEF DESCRIPTION OF THE DRAWING

FIG. 4 is a diagramatic view of the probe.

FIG. 5 is a diagrammatic view of one pyramidal tip.

FIG. 6 is a cross-sectional view of the pyramidal tip of FIG. 5 with a spherical silver particle attached.

FIG. 7 is a diagrammatic view of a second pyramidal tip.

FIG. 8 is a cross-sectional view of the pyramidal tip of FIG. 7 with an ellipsoidal particle attached.

DESCRIPTION OF THE PREFERRED EMBODIMENTS

Figure 1:
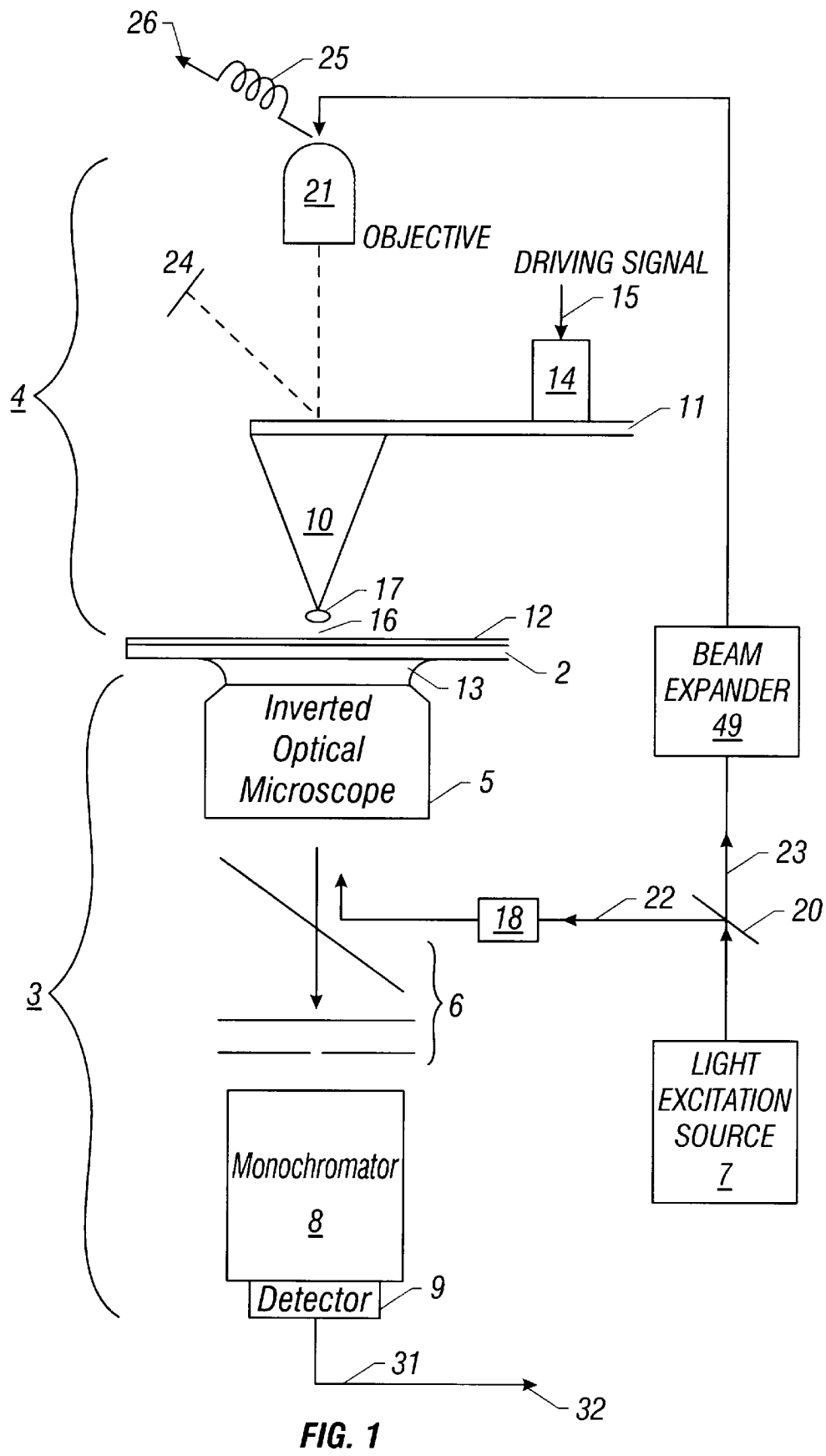
FIG. 1 is a schematic diagram of the high resolution scanning Raman microscope.

Referring to FIG. 1, a high resolution Raman microscope consists of a mobile stage 2, with x-y-z movement capability, a surface enhanced Raman scattering microscope (SERS) 3, placed beneath the stage 2, and an atomic force microscope (AFM) 4, placed on top of the stage 2. The sample 16 is placed on a transparent cover slip 12, and mounted on top of the stage 2, which has an aperture 13 allowing the excitation light and the optical image signal to pass through. The cover slip 12 with the sample is mounted directly above the aperture 13 of the stage 2.

The AFM 4 consists of a probe 10, a cantilever 11, supporting the probe, a piezo-electric stack 14, a driving signal 15, and electronics for signal detection and correction. The probe 10 has a pyramidal shape and the tip of the pyramid is coated with silver particles 17.

The SERS consists of an inverted optical microscope 5, mounted immediately beneath the stage 2, confocal optics 6, a light excitation source 7, a monochromator 8, for the spectral dissociation of the optical signal, and a detector system 9.

The excitation light is generated by either a Nd:YAG laser for the 532 nm wavelength or a Ti:sapphire laser for the 365 nm wavelength. Pulsed laser beams can be used as well as continuous beams. The light excitation signal passes through a 50–50% beam splitter 20, generating two light beams, the sample excitation signal 22 and the reference signal for the height detection 23. The sample excitation signal 22 passes through a beam expander 18 and through the confocal optics 6 and the microscope objective 5, and is focused onto the sample 16. The light emitted from the sample is collected by the microscope objective 5, the confocal optics 6, and is coupled to the monochromator 8 for spectral dissociation. The confocal optics 6 includes a combination of dichroic filters, barrier filters, confocal pinholes, lenses, and mirrors, and serves the purpose of reducing the background signal. Standard full field optics can be used as well as confocal optics. The signal with the spectroscopic information is detected by the detector system 9. The detector system 9 includes an avalanche photodiode interfaced with a computer for counting and digitization of the signal. The reference light beam 23 passes through a beam expander 19 and a microscope objective 21, and is coupled to the AFM height detection system (53) through an optical fiber 25.

Figure 2:
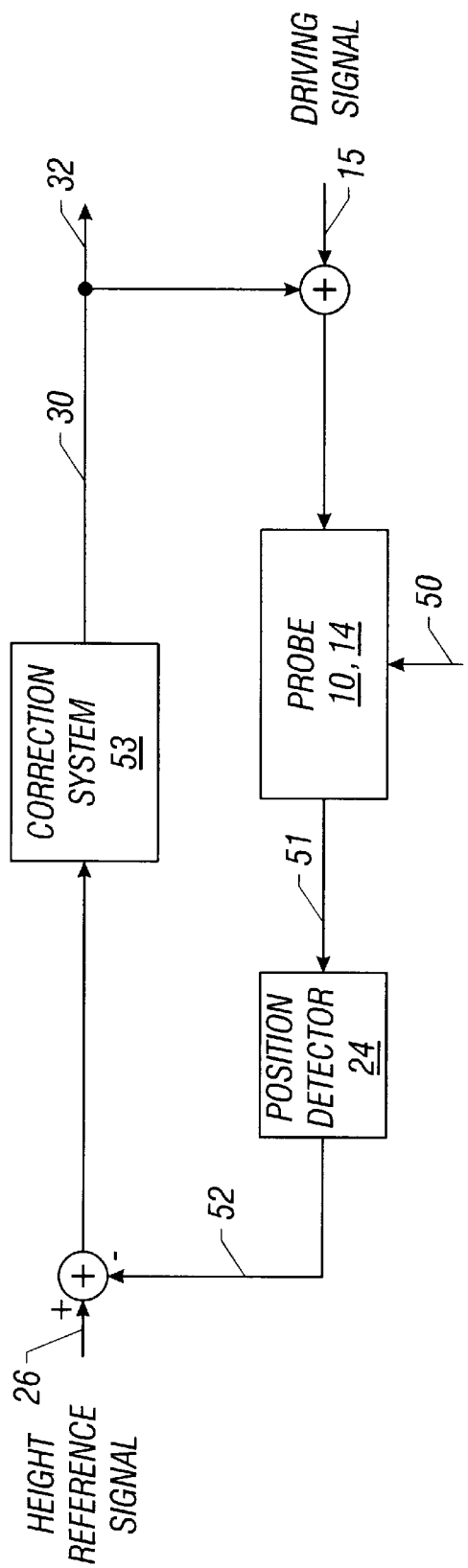
FIG. 2 is a functional block diagram of the atomic force microscope.

The functional block diagram for the AFM is shown in FIG. 2. A sinusoidal diving signal 15 is coupled to the AFM probe 10 via the piezo-electric stack 14. The AFM probe 10 is scanned over the surface of the sample 16, receiving the perturbations (50) caused by the surface of the sample and transmitting the perturbed signal (51) to a position detector 24. The position detector 24 transmits a position signal 52 to electronic systems for correcting (53) and digitizing (32) the signal. The correction occurs by comparing the position signal to an external height reference signal 26.

Figure 3:
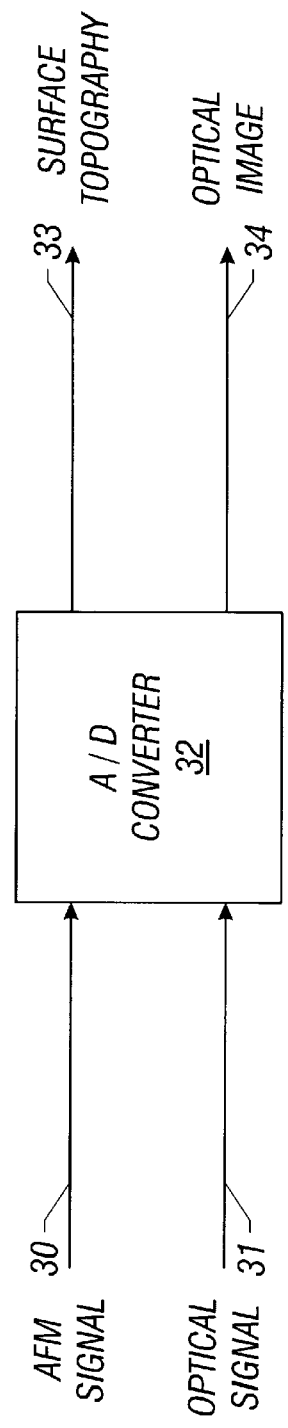
FIG. 3 is a block diagram of the digitizing system.

Referring to FIG. 3, both the corrected AFM signal 30 and the optical signal 31 are coupled to the digitizing system (32) for the processing of the AFM image 33 of the surface topography and the optical image 34.

Referring to FIGS. 4–9, the probe 10 carries a conductive element 1, which, for example, can be a metallic coating (FIG. 4) or a conductive particle (FIGS. 5–9).

Referring to FIGS. 5 and 7 the AFM probe 10 has a pyramidal structure with silver particles 17 attached at the tip of the pyramid. Depending upon the dimensions of the base of the pyramid, a spherical particle (FIG. 5), or an ellipsoidal particle (FIG. 7) is formed. FIGS. 6 and 8 show the cross-sectional area 39 of the probe 10, near the tip, with the silver particles 17 attached.

Figure 9:
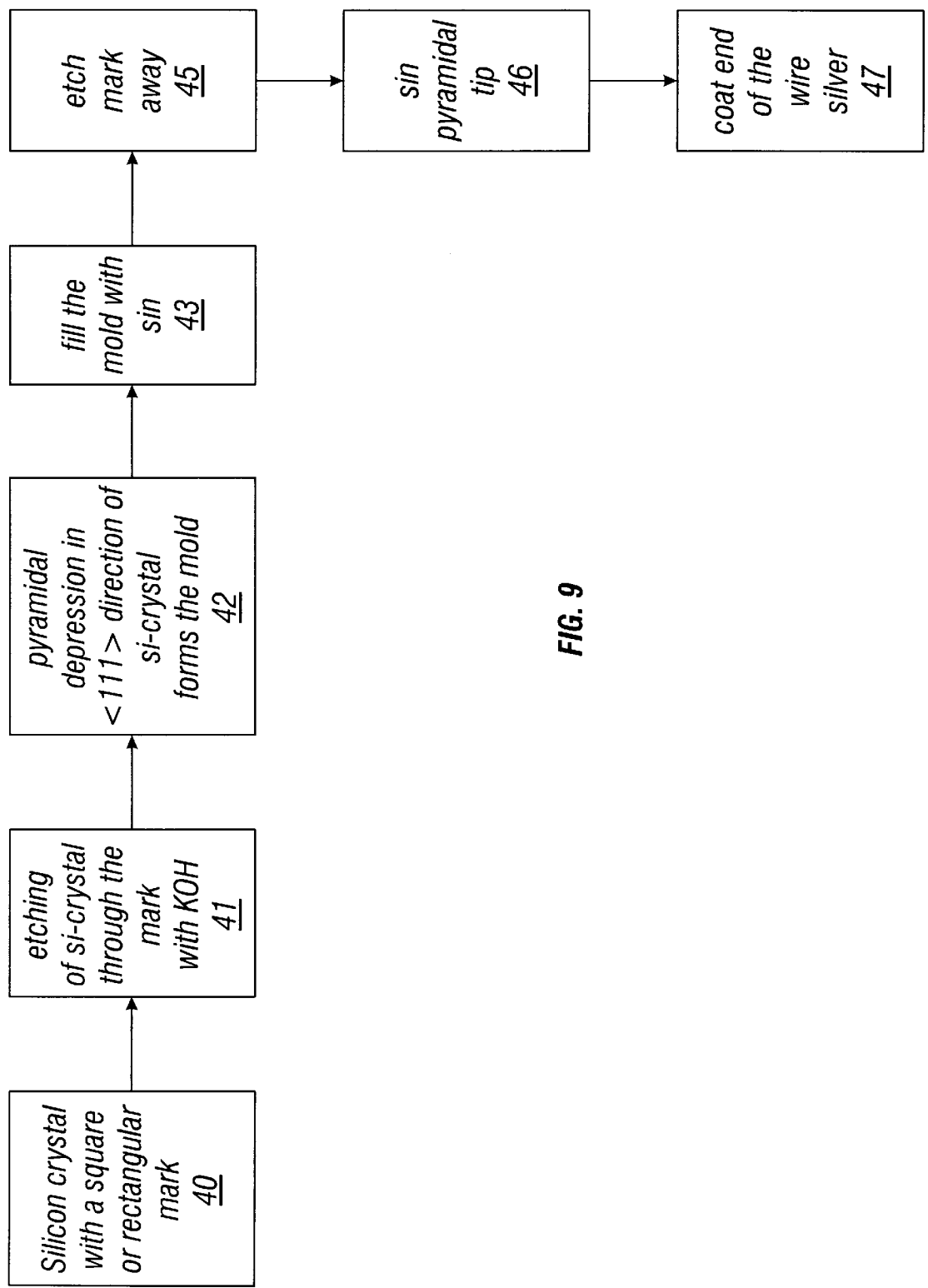
FIG. 9 is process diagram for fabricating an AFM probe.

Referring to FIG. 9, the process of fabricating an AFM probe 10 with spherical or ellipsoidal symmetry includes the steps of forming a mold in a silicon crystal (42), filling the mold with SiN (43), and etching the silicon mask away (45), leaving behind a pyramidal shaped probe(46) and finally coating the tip with silver particles (47).

The mold is formed in the silicon crystal by preferentially etching (41) the silicon crystal through a mask with an etchant such as KOH. The mask may have the shape of a square for a tip with spherical symmetry or rectangle for a tip with ellipsoidal symmetry. The etching process etches away preferentially the (110) and (100) surfaces leaving a pyramidal depression in the <111> direction (42). This pyramidal depression constitutes the mold, which is filled with SiN (43). With a rectangular mask a tip with spherical symmetry is formed with a radius of curvature of approximately 20 nm. For an ellipsoidal tip a rectangle mask is used wherein the aspect ratio of the rectangle determine the aspect ratio of the tip. The tip is then coated with a layer of silver (47). Typical thicknesses for the silver layer are in the range of 10 to 20 nm.

The ellipsoid tip manufactured by this method is an oblate. The oblate ellipsoidal tip has lower enhancement than the prolate ellipsoid. However, by aligning the tip at an angle of approximately 20 degrees away from the line perpendicular to the sample surface, the smaller radius of curvature of the ellipsoid is oriented towards the sample. In other embodiments of the invention, the conductive metallic particles can be gold, platinum, aluminum, or copper among others. In addition to single type metallic particles, the probe can be coated with multiple metallic layers or particles such as gold over silver or copper over aluminum, among others. The metallic particle can be in colloidal form and can be attached to the probe by surface adhesion forces.

The principles of operation of the high resolution scanning Raman microscope are described next. Conducting particles smaller than the wavelength of light have a surface plasmon resonance that can be excited by incident light. The particle can absorb the photon, and will store the energy in the surface plasmon resonance. This energy is localized in the direction perpendicular to the surface of the sphere. Thus, a Raman scattering particle near the surface of the conducting particle will have an enhanced excitation field. Since the surface plasmon resonance has a dipole symmetry, it can radiate. Thus, the emitted field is also enhanced. Simple models for SERS solve LaPlace's equation for a Raman scattering particle near a perfect conductor of spherical or ellipsoidal geometry.

The conducting particle can be replaced by a point dipole of magnitude $$\alpha_e = -1/3\ ab^2\ [(\epsilon_0 - \epsilon(\omega))/(\epsilon_0 - A(\epsilon_0 - \epsilon(\omega)))] \quad (1)$$

where $\epsilon(\omega)$ and $\epsilon_0$ are the dielectric constants of the metal and the surrounding medium, respectively, and A is a geometrical depolarization factor. For a sphere A=1/3 and for an ellipsoid with 3:1 aspect ratio A=0.1. Equation (1) has a resonance at $\epsilon(\omega) = \epsilon_0(1-1/A)$. Silver satisfies these conditions with visible light, since the imaginary part of $\epsilon(\omega)$ is small and the real part ranges from −2 to −20 over 350–700 nm.

On resonance, the induced dipole field of the particle is large, increasing the Raman polarization and molecular dipole moment of the Raman scattering particle. The emitted Raman-scattered radiation also induces a dipole field on the metallic particle, so the emitted radiation is also enhanced. Since both the incoming and outgoing electric fields are enhanced, the effect comes as a squared power, and the dipole radiation is enhanced by $f \sim (\alpha_e/r^3)^2$. But the intensity one observes is the square of the electric field, so that the final effect goes as the fourth power of the resonance singularity:

$$|f|^2 \sim \alpha_e^4/r^{12} \quad (2)$$

Note that the effect falls off as the 12th power of the distance of the Raman scattering particle from the metallic sphere; this is what provides high resolution for the microscope.

The location and size of the enhancement depends on the aspect ratio of the ellipsoid. Spherical particles have a $10^6$ enhancement, centered around 360 nm. Ellipsoids with an aspect ratio of 3:1 have a $10^7$ enhancement in the more convenient region of 550 nm. The geometry of the probe thus has a strong effect on the location and size of the resonance.

One can calculate the expected signal size for the test case of CN, whose Raman cross section is about $3 \times 10^{-30}$ cm$^2$. Assuming an incident beam of 1 mW visible light focused to the diffraction limit, the (unenhanced) Raman signal from a single CN molecule is $3 \times 10^{-6}$ photons/sec. With a typical enhancement of $10^7$, one would have a signal of 30 photons/sec. This is difficult to detect, but feasible as it was demonstrated by Nie et al. and Kneip et al.

A fluorophore will only emit a finite number of photons ($10^5$–$10^6$) before becoming irreversibly photobleached. Raman scattering does not suffer from this problem, since the quantum chemistry of the system is typically much more simple. One simply excites a vibrational mode of the molecule, which relaxes to the ground state in picoseconds. Even though the cross-section is much smaller than for fluorescent dye molecules, the faster relaxation time makes up some of the difference by allowing a higher repetition rate.

The resolution of the microscope is determined solely by the tip size, i.e., the size of the conductive element at the tip. From equation (2), the enhancement falls off as a high power of the distance of the Raman scatterer from the tip, with respect to the tip size. The enhancement as a function of distance from the tip is $|f|^2 \sim (ab^2/r^3)^4$. The resolution is calculated by using the Rayleigh criterion: the full width half max of equation (2) with respect to r is approximately 0.35 R, where $R=(ab_2)^{1/3}$ is the geometric mean radius of curvature of the surface of the conductive element at the tip. Standard AFM tips have a radius of curvature of about 20 nm, giving a projected resolution of 7 nm, or 70 Angstroms.

In building the microscope several other points are considered. These include the wavelength used to excite the Raman scattering, and the geometry and size of the probe.

While the easiest probe to make is spherical (one could just coat an AFM tip with silver), the resonance is smaller and narrower than for ellipsoids. More importantly, the wavelength is in the near-ultraviolet at 365 nm. A doubled Ti:sapphire laser could be used to generate excitation light in that regime, and would have the advantage that it is tunable. However, the disadvantage is that one runs into autofluorescence of contaminants and substrates. One also has to work with more expensive optics and detectors, not to mention the high cost of the laser. Since most biological molecules have absorption lines in the ultraviolet spectral region, one runs the risk of destroying the molecule of interest. Thus, the most conservative approach, scientifically and economically, is to fabricate an ellipsoidal probe.

Several strategies are employed to accomplish this. The first is to randomly roughen a silver-coated AFM tip with the same electrochemical method used in bulk SERS electrodes. One then finds a surface feature of the proper size and geometry (e.g., sufficiently small radius of curvature) on the conductive coating at the end of the tip, much as in the development of the first STM tips. The second, and more controlled, method is to explicitly manufacture ellipsoidal AFM tips according to the process described in FIG. 9.

Another method to manufacture a prolate ellipsoid is to use electron beam deposition to grow carbon deposit on a standard silicon nitride pyramidal tip. In this way the desired aspect ratio is obtained and then a 10–20 nm layer of silver is evaporated onto the tip. One can thus make an AFM tip with SERS resonance near 550 nm, which demonstrates SERS enhancement of $10^7$. The tip is excited with 532 nm light from a solid state frequency doubled Nd:YAG laser.

This device uses far field optics and photon counting detection methods to further increase the sensitivity of the detection signal. Photon counting avalanche photodiodes have dark currents as low as 7 counts/sec, are relatively cheap, and have high quantum efficiency (70%). The fluorescence spectrum is measured with a monochromator, inserted in the beam path. The pulses from the avalanche photodiode are counted and digitized by a computer. Another possible detection scheme includes a diffraction grating and an image intensified charged coupled device (CCD) camera or a cooled CCD camera.

Another embodiment of this invention is the method of utilizing the high resolution Raman microscope to detect and measure the optical properties of single as well as small number molecules for in situ diagnostic purposes. Specifically this method is applied in measuring in situ the chemical composition of electronic devices as part of a quality control procedure, screening biological molecules, DNA sequencing and ultra low level chemical detection applications.

For DNA sequencing, the instrument obtains images of the four DNA bases. The SERS signals from the individual bases are distinguishable from the bulk DNA SERS spectrum. Since the individual DNA bases are distinguished a molecule of DNA is sequenced by scanning the tip along its length. Single base resolution is 3 Angstroms and the instrument resolution with the carbon nano-tube tip is 7 Angstroms. However, the bases are detected in pairs from a molecule of single stranded DNA and the single base is identified by the fact that there is a common element between adjacent pairs.

The method can also be applied in fluorescent dye molecules, but with not as high enhancement. Ultra high resolution fluorescence microscopy is achieved in this way.

In another embodiment of this invention, the AFM probe operates in a tapping mode, and lock-in detection techniques are applied. The tapping frequency signal of the AFM probe modulates the detection signal resulting in increased sensitivity.

Other embodiments include systems which control the distance between the probe and the surface of the sample.

Other embodiments are within the scope of the following claims.

What is claimed is:

1. A scanning microscope for obtaining high-resolution spectroscopic information, the microscope comprising:
   a support stage, having surfaces for supporting a sample;
   a first optical apparatus for directing an optical beam at the sample;
   a second optical apparatus for collecting light emitted from the sample to reduce the background noise;
   a spectral dissociating apparatus coupled to said second optical apparatus to dissociate light emitted from the sample for analysis;
   a probe supporting a conductive element at a location within the optical beam area, the conductive element being configured to enhance emission of light from molecules in the vicinity of the conductive element; and
   a probe height detection apparatus operatively connected with said probe to generate detection signals representing surface topography, said probe height detection apparatus detecting a change in surface profile by differencing a reference beam from a reflected signal of the reference beam.

2. The scanning microscope of claim 1, wherein the second optical apparatus is a spectrometer.

3. The scanning microscope of claim 1, wherein the emitted light is Raman scattered light.

4. The scanning microscope of claim 1, wherein the emitted light is fluorescence.

5. The scanning microscope of claim 3 or 4, wherein the area illuminated by the optical beam is greater than the area in which enhancement occurs in the vicinity of the conductive element.

6. The scanning microscope of claim 3 or 4, wherein the area illuminated by the optical beam is at least ten times greater than the area in which enhancement occurs in the vicinity of the conductive element.

7. The scanning microscope of claim 1, wherein the distance between the conductive element and the surface of the sample is controlled.

8. The scanning microscope of claim 7, wherein the probe is an atomic force microscope probe.

9. The scanning microscope of claim 1, wherein the support stage has a three dimensional scanning capability.

10. The scanning microscope of claim 1, wherein the surface of the conductive element has a curvature of less than or equal to 20 nm.

11. The scanning microscope of claim 1, wherein the probe comprises carbon nanotubes with a radius of curvature of less or equal to 5 nm.

12. The scanning microscope of claim 1, wherein the probe has pyramidal geometry.

13. The scanning microscope of claim 1, wherein the probe comprises silicon nitride.

14. The scanning microscope of claim 1, wherein the the conductive element comprises a conductive layer.

15. The scanning microscope of claim 14, wherein the conductive layer comprises a conductive particle.

16. The scanning microscope of claim 15, wherein the conductive particle is a sphere.

17. The scanning microscope of claim 15, wherein the conductive particle is an ellipsoid.

18. The scanning microscope of claim 15, wherein the conductive particle is a silver particle.

19. The scanning microscope of claim 1, wherein a photon counting avalanche photodiode is used to detect the optical signal.

20. The scanning microscope of claim 2, wherein the spectrometer comprises a diffraction grating and an image intensified charged coupled device (CCD) camera.

21. The scanning microscope of claim 1, wherein the probe oscillates in a tapping frequency which is used to modulate the detection signals generated by said probe height detection apparatus, such that the modulation increases probe sensitivity and operates to generate enhanced-quality surface topography.

22. The scanning microscope of claim 20, wherein the CCD camera is cooled.

23. The scanning microscope of claim 14, wherein the conductive element comprises a colloidal silver particle attached by surface adhesion forces.

24. The scanning microscope of claim 14, wherein the conductive element comprises metal particles selected from the group consisting of silver, gold, platinum, copper, and aluminum.

25. The scanning microscope of claim 14, wherein the conductive element comprises multiple metallic layers.

26. The scanning microscope of claim 1, wherein the probe comprises single crystalline silicon.

27. The scanning microscope of claim 1, wherein the probe comprises carbon.

28. The scanning microscope of claim 1, further comprising:
   a detection system coupled to said spectral dissociating apparatus, said detection system receiving spectroscopic information of the dissociated light and generating optical image of the sample.

29. The scanning microscope of claim 1, wherein said second optical apparatus includes filters, pinholes, lenses, and mirrors.

30. A method of obtaining high-resolution spectroscopic and surface topographic information of a sample, the method comprising:
   supporting the sample on a support stage;
   directing an optical beam at the sample;
   collecting light emitted from the sample through a series of filtering mechanisms to reduce the background noise;

spectrally dissociating light emitted from the sample;

supporting a conductive element from a probe at a location within the optical beam area, the conductive element being configured to enhance the light emitted from molecules in the vicinity of the conductive element;

generating a reference beam using a laser and coupling the reference beam to the probe;

receiving perturbations of the reference beam caused by the surface of the sample from the probe and transmitting the perturbations as a reflected signal; and generating surface topography by differencing the reference beam from the reflected signal.

31. The method of claim 30, wherein the light emitted from the sample is Raman scattering.

32. The method of claim 30, wherein the light emitted from the sample is fluorescence.

33. The method of claim 30, wherein the area illuminated by the optical beam is greater than the area in which enhancement occurs in the vicinity of the conductive element.

34. The method of claim 30, wherein the area illuminated by the optical beam is at least ten times greater than the area in which enhancement occurs in the vicinity of the conductive element.

35. The method of claim 30, wherein the distance between the conductive element and the surface of the sample is controlled.

36. The method of claim 30, wherein the probe is an atomic force microscope probe.

37. The method of claim 30, wherein the support stage has a three dimensional scanning capability.

38. The method of claim 30, wherein the surface of the conductive element has a curvature of less than or equal to 20 nm.

39. The method of claim 30, wherein the probe comprises carbon nanotubes with a radius of curvature of less or equal to 5 nm.

40. The method of claim 30, wherein the probe has pyramidal geometry.

41. The method of claim 30, wherein the probe comprises silicon nitride.

42. The method of claim 30, wherein the the conductive element comprises a conductive layer.

43. The method of claim 42, wherein the conductive layer comprises a conductive particle.

44. The method of claim 43, wherein the conductive particle is a sphere.

45. The method of claim 43, wherein the conductive particle is an ellipsoid.

46. The method of claim 43, wherein the conductive particle is a silver particle.

47. The method of claim 30, wherein a photon counting avalanche photodiode is used to detect the optical signal.

48. The method of claim 30, wherein a spectrometer directs the optical beam and the spectrometer comprises a diffraction grating and an image intensified charged coupled device (CCD) camera.

49. The method of claim 30 applied to sequencing DNA by obtaining surface enhanced Raman scattering images of the four individual DNA bases.

50. The method of claim 31 applied to performing in situ diagnostic quality control of nanostructural electronic devices by scanning the probe over the surface of the nanostructures and obtaining surface enhanced Raman scattering spectra.

51. The method of claim 31 applied to detecting ultra-low level chemical components in a mixture by obtaining surface enhanced Raman scattering spectra.

52. The method of claim 30, further comprising:

generating optical image of the sample by using spectroscopic information of the dissociated light.

* * * * *